United States Patent
Piscopio et al.

(10) Patent No.: US 6,509,337 B1
(45) Date of Patent: Jan. 21, 2003

(54) ARYLSULFONYL HYDROXAMIC ACID DERIVATIVES AS MMP AND TNF INHIBITORS

(75) Inventors: Anthony Piscopio, Longmount, CO (US); James P. Rizzi, Niwot, CO (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/154,969

(22) Filed: Sep. 17, 1998

Related U.S. Application Data

(62) Division of application No. 08/930,665, filed as application No. PCT/IB95/00279 on Oct. 7, 1997, now Pat. No. 5,861,510.

(51) Int. Cl.[7] ................. A61K 31/445; A61K 31/4965; A61K 31/54; C07D 211/96; C07D 241/04
(52) U.S. Cl. ............... 514/237.5; 514/252.12; 514/255.02; 514/318; 514/330; 544/131; 544/159; 544/383; 544/384; 546/194; 546/225
(58) Field of Search .................. 544/131, 159, 544/383, 384; 514/237.5, 252.12, 255.02, 318, 330; 546/194, 225

(56) References Cited

U.S. PATENT DOCUMENTS

| | | | | |
|---|---|---|---|---|
| 5,753,653 A | * | 5/1998 | Bender et al. | 514/227.5 |
| 5,861,510 A | * | 1/1999 | Piscopio et al. | 544/131 |
| 6,121,258 A | * | 9/2000 | Pikul et al. | 514/218 |
| 6,130,220 A | * | 10/2000 | Broka et al. | 514/255.01 |
| 6,143,744 A | * | 11/2000 | Broka et al. | 514/238.2 |
| 6,153,757 A | * | 11/2000 | Zook et al. | 546/301 |
| 6,166,005 A | * | 12/2000 | De et al. | 514/211.01 |
| 6,225,311 B1 | * | 5/2001 | Levin et al. | 514/227.5 |
| 6,329,397 B1 | * | 12/2001 | McClure et al. | 514/330 |

FOREIGN PATENT DOCUMENTS

| | | |
|---|---|---|
| EP | 606046 | 7/1994 |

* cited by examiner

*Primary Examiner*—Richard L. Raymond
(74) *Attorney, Agent, or Firm*—Peter C. Richardson; Paul H. Ginsburg; Pamela C. Ancona

(57) ABSTRACT

A compound of the formula

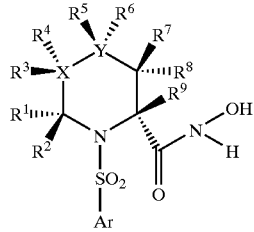

wherein $R^1$–$R^9$ and Ar are as defined above, useful in the treatment of a condition selected from the group consisting of arthritis, cancer, tissue ulceration, restenosis, periodontal disease, epidemrolysis bullosa, scleritis and other disease characterized by matrix metalloproteinase activity, as well as AIDS, sepsis, septic shock and other diseases involving the production of TNF.

8 Claims, No Drawings

ARYLSULFONYL HYDROXAMIC ACID DERIVATIVES AS MMP AND TNF INHIBITORS

This application is a divisional Ser. No. 08/930,665 filed Oct. 7, 1997, now U.S. Pat. No. 5,861,510, which is a 371 of PCT/IB 95/00279 filed Apr. 20, 1995.

BACKGROUND OF THE INVENTION

The present invention relates to arylsulfonyl hydroxamic acid derivatives which are inhibitors of matrix metalloproteinases or the production of tumor necrosis factor (hereinafter also referred to as TNF) and as such are useful in the treatment of a condition selected from the group consisting of arthritis, cancer, tissue ulceration, restenosis, periodontal disease, epidermolysis bullosa, sceritis and other diseases characterized by matrix metalloproteinase activity, as well as AIDS, sepsis, septic shock and other diseases involving the production of TNF.

This invention also relates to a method of using such compounds in the treatment of the above diseases in mammals, especially humans, and to the pharmaceutical compositions useful therefor.

There are a number of enzymes which effect the breakdown of structural proteins and which are structurally related metalloproteases. Matrix-degrading metalloproteinases, such as gelatinase, stromelysin and collagenase, are involved in tissue matrix degradation (e.g. collagen collapse) and have been implicated in many pathological conditions involving abnormal connective tissue and basement membrane matrix metabolism, such as arthritis (e.g. osteoarthritis and rheumatoid arthritis), tissue ulceration (e.g. corneal, epidermal and gastric ulceration), abnormal wound healing, periodontal disease, bone disease (e.g. Paget's disease and osteoporosis), tumor metastasis or invasion, as well as HIV-infection (*J. Leuk. Biol.*, 52 (2): 244–248, 1992).

Tumor necrosis factor is recognized to be involved in many infectious and auto-immune diseases (W. Friers, *FEBS Letters*, 1991, 285, 199). Furthermore, it has been shown that TNF is the prime mediator of the inflammatory response seen in sepsis and septic shock (C. E. Spooner et al., *Clinical Immunology and Immunopathology*, 1992, 62 S11).

SUMMARY OF THE INVENTION

The present invention relates to a compound of the formula

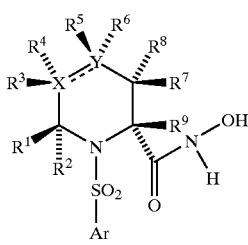

I or the pharmaceutically acceptable salt thereof, wherein the broken line represents an optional double bond;

Y is carbon, oxygen, sulfur, sulfoxide, sulfone or nitrogen;

$R^1$, $R^2$, $R^3$, $R^4$, $R^5$, $R^6$, $R^7$, $R^8$ and $R^9$ are selected from the group consisting of hydrogen, $(C_1-C_6)$alkyl optionally substituted by $(C_1-C_6)$alkylamino, $(C_1-C_6,)$alkylthio, $(C_1-C_6)$alkoxy, trifluoromethyl, $(C_6-C_{10})$aryl, $(C_5-C_9)$heteroaryl, $(C_6-C_{10})$arylamino, $(C_6-C_{10})$arylthio, $(C_6-C_{10})$aryloxy, $(C_5-C_9)$heteroarylamino, $(C_5-C_9)$heteroarytti, $(C_5-C_9)$heteroaryloxy, $(C_6-C_{10})$aryl$(C_6-C_{10})$aryl, $(C_3-C_6)$cycloalykyl, hydroxy $(C_1-C_6)$alkyl, $(C_1-C_6)$alkyl(hydroxymethylene), piperazinyl,$(C_6-C_{10})$aryl$(C_1-C_6)$alkoxy,$(C_5-C_9)$heteroaryl$(C_1-C_6)$alkoxy, $(C_1-C_6)$acylamino, $(C_1-C_6)$acylthio, $(C_1-C_6)$acyloxy, $(C_1-C_6)$alkylsulfinyl, $(C_6-C_{10})$arylsulfinyl, $(C_1-C_6)$alkylsulfonyl, $(C_6-C_{10})$arylsulfonyl, amino, $(C_1-C_6)$alkylamino or $((C_1-C_6)$alkylamino$)_2$; $(C_2-C_6)$alkenyl, $(C_6-C_{10})$aryl$(C_2-C_6)$alkenyl, $(C_5-C_9)$heteroaryl$(C_2-C_6)$alkenyl, $(C_2-C_6)$alkynyl, $(C_6-C_{10})$aryl$(C_2-C_6)$alkynyl, $(C_5-C_9)$heteroaryl$(C_2-C_6)$alkynyl, $(C_1-C_6)$alkylamino, $(C_1-C_6)$alkylthio, $(C_1-C_6)$alkoxy, trifluoromethyl, $(C_1-C_6)$alkyl(difluoromethylene), $(C_1-C_3)$alkyl(difluoromethylene)$(C_1-C_3)$alkyl, $(C_6-C_{10})$aryl, $(C_5-C_9)$heteroaryl, $(C_6-C_{10})$arylamino, $(C_6-C_{10})$arylthio, $(C_6-C_{10})$aryloxy, $(C_5-C_9)$heteroarylamino, $(C_5-C_9)$heteroarytthio, $(C_5-C_9)$heteroaryloxy, $(C_3-C_6)$cycloalkyl, $(C_1-C_6)$alkyl(hydroxymethylene), piperidyl, $(C_1-C_6)$alkylpiperidyl, $(C_1-C_6)$acylamino, $(C_1-C_6)$acylthio, $(C_1-C_6)$acyloxy, $R^{13}(C_1-C_6)$alkyl wherein $R^{13}$ is $(C_1-C_6)$acylpiperazino, $(C_6-C_{10})$arylpiperazino, $(C_5-C_9)$heteroarylpiperazino, $(C_1-C_6)$alkylpiperazino, $(C_1-C_{10})$aryl$(C_1-C_6)$alkylpiperazino, $(C_5-C_9)$heteroaryl$(C_1-C_6)$alkylpiperazino,morpholino, thiomorpholino, piperidino, pyrrolidino, piperidyl, $(C_1-C_6)$alkylpiperidyl, $(C_6-C_{10})$arylpiperidyl, $(C_5-C_9)$heteroarylpiperidyl, $(C_1-C_6)$alkylpiperidyl$(C_1-C_6)$alkyl, $(C_6-C_{10})$arylpiperidyl$(C_1-C_6)$alkyl, $(C_5-C_9)$heteroarylpiperidyl$(C_1-C_6)$alkyl or $(C_1-C_6)$acylpiperidyl;

or a group of the formula

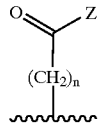

wherein n is 0 to 6;

Z is hydroxy, $(C_1-C_6)$alkoxy or $NR^{14}R^{15}$ wherein $R^{14}$ and $R^{15}$ are each independently selected from the group consisting of hydrogen, $(C_1-C_6)$alkyl optionally substituted by $(C_1-C_6)$alkylpiperidyl, $(C_6-C_{10})$arylpiperidyl, $(C_5-C_9)$heteroarylpiperidyl, $(C_6-C_{10})$aryl, $(C_5-C_9)$heteroaryl, $(C_6-C_{10})$aryl$(C_6-C_{10})$aryl or $(C_3-C_6)$cycloalkyl; piperidyl, $(C_1-C_6)$alkylpiperidyl, $(C_6-C_{10})$arylpiperidyl, $(C_5-C_9)$heteroarylpiperidyl, $(C_1-C_6)$acylpiperidyl, $(C_6-C_{10})$aryl, $(C_5-C_9)$heteroaryl, $(C_6-C_{10})$aryl$(C_6-C_{10})$aryl $(C_3-C_6)$cycloalkyl, $R^{16}(C_2-C_6)$alkyl, $(C_1-C_5)$alkyl $(CHR^{16})(C_1-C_6)$alkyl wherein $R^{16}$ is hydroxy, $(C_1-C_6)$acyloxy, $(C_1-C,)$alkoxy, piperazino, $(C_1-C_6)$acylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfoxyl, $(C_6-C_{10})$arylsulfoxyl, amino, $(C_1-C_6)$alkylamino, $((C_1-C_6)$alkyl$)_2$amino, $(C_1-C_6)$acylpiperazino, $(C_1-C_6)$alkylpiperazino, $(C_6-C_{10})$aryl$(C_1-C_6)$alkylpiperazino, $(C_5-C_9)$heteroaryl$(C_1-C_6)$alkylpiperazino,morpholino, thiomorpholino, piperidino or pyrrolidino; $R^{17}$ $(C_1-C_6)$alkyl, $(C_1-C_5)$alkyl$(CHR^{17})(C_1-C_6)$alkyl wherein $R^{17}$ is piperidyl or $(C_1-C_6)$alkylpiperidyl; and $CH(R^{18})COR^{19}$ wherein $R^{18}$ is hydrogen, $(C_1-C_6)$alkyl, $(C_6-C_{10})$aryl$(C_1-C_6)$alkyl, $(C_5-C_9)$heteroaryl$(C_1-C_6)$alkyl, $(C_1-C_6)$alkylthio$(C_1-C_6)$alkyl, $(C_6-C_{10})$arylthio$(C_1-C_6)$alkyl, $(C_1-C_6)$alkylsulfinyl$(C_1-C_6)$alkyl, $(C_6-C_{10})$arylsulfinyl$(C_1-C_6)$alkyl, $(C_1-C_6)$alkylsulfonyl$(C_1-C_6)$alkyl, $(C_6-C_{10})$arylsulfonyl$(C_1-C_6)$alkyl, hydroxy$(C_1-C_6)$alkyl, amino$(C_1-C_6)$alkyl, $(C_1-C_6)$alkylamino$(C_1-C_6)$alkyl, $((C_1-C_6)$alkylamino$)_2(C_1-C_6)$alkyl, $R^{20}R^{21}NCO(C_1-C_6)$alkyl or $R^{20}OCO(C_1-C_6)$alkyl wherein $R^{20}$ and $R^{21}$ are each independently selected from the group consisting of hydrogen, $(C_1-C_6)$alkyl, $(C_6-C_{10})$aryl$(C_1-C_6)$alkyl and $(C_5-C_9)$heteroaryl$(C_1-C_6)$alkyl; and $R^{19}$ is $R^{22}O$ or $R^{22}R^{23}N$ wherein $R^{22}$ and $R^{23}$ are each independently selected from the group consisting of hydrogen, $(C_1-C_6)$alkyl, $(C_6-C_{10})$aryl$(C_1-C_6)$alkyl and $(C_5-C_9)$heteroaryl$(C_1-C_6)$alkyl;

or $R^{14}$ and $R^{15}$, or $R^{20}$ and $R^{21}$, or $R^{22}$ and $R^{23}$ may be taken together to form an azetidinyl, pyrrolidinyl, morpholinyl, thiomorpholinyl, indolinyl, isoindolinyl, tetrahydroquinolinyl, tetrahydroisoquinolinyl, $(C_1-C_6)$acylpiperazinyl, $(C_1-C_6)$alkylpiperazinyl, $(C_6-C_{10})$arylpiperazinyl, $(C_5-C_9)$heteroarylpiperazinyl or a bridged diazabicydoalkyl ring selected from the group consisting of

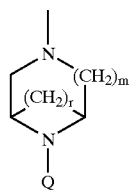

a

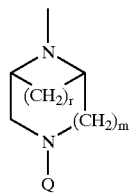

b

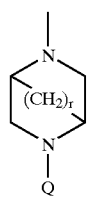

c

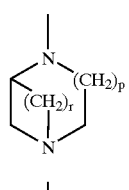

d

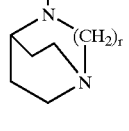

e wherein
r is 1, 2 or 3;

m is 1 or 2;
p is 0 or 1; and
Q is hydrogen, $(C_1-C_3)$alkyl, $(C_1-C_6)$acyl or $(C_1-C_6)$alkoxy carbamoyl;

or $R^1$ and $R^2$, or $R^3$ and $R^4$, or $R^5$ and $R^6$ may be taken together to form a carbonyl;

or $R^1$ and $R^2$, or $R^3$ and $R^4$, or $R^5$ and $R^6$, or $R^7$ and $R^8$ may be taken together to form a $(C_3-C_6)$cycloalkyl, oxacyclohexyl, thiocyclohexyl, indanyl or tetralinyl ring or a group of the formula

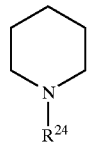

wherein
$R^{24}$ is hydrogen, $(C_1-C_6)$acyl, $(C_1-C_6)$alkyl, $(C_6-C_{10})$aryl$(C_1-C_6)$alkyl, $(C_5-C_9)$heteroaryl$(C_1-C_6)$alkyl or $(C_1-C_6)$alkylsulfonyl; and Ar is $(C_6-C_{10})$aryl or $(C_5-C_9)$heteroaryl, each of which may be optionally substituted by $(C_1-C_6)$alkyl, one or two $(C_1-C_6)$alkoxy, $(C_6-C_{10})$aryloxy or $(C_5-C_9)$heteroaryloxy;

with the proviso that $R^7$ is other than hydrogen only when $R^8$ is other than hydrogen;

with the proviso that $R^6$ is other than hydrogen only when $R^5$ is other than hydrogen;

with the proviso that $R^3$ is other than hydrogen only when $R^4$ is other than hydrogen;

with the proviso that $R^2$ is other than hydrogen only when $R^1$ is other than hydrogen;

with the provisio that when $R^1$, $R^2$ and $R^9$ are a substituent comprising a heteroatom, the heteroatom cannot be directly bonded to the 2- or 6-positions;

with the proviso that when X is nitrogen, $R^4$ is not present;

with the proviso that when X is oxygen, sulfur, sulfoxide, sulfone or nitrogen and when one or more of the group consisting of $R^1$, $R^2$, $R^5$ and $R^6$, is a substituent comprising a heteroatom, the heteroatom cannot be directly bonded to the 4- or 6-positions;

with the proviso that when Y is oxygen, sulfur, sulfoxide, sufone or nitrogen and when one or more of the group consisting of $R^3$, $R^4$, $R^7$ and $R^8$, are independently a substituent comprising a heteroatom, the heteroatom cannot be directly bonded to the 3- or 5-positions;

with the proviso that when X is oxygen, sulfur, sulfoxide or sulfone, $R^3$ and $R^4$ are not present;

with the proviso that when Y is nitrogen, $R^4$ is not present;

with the proviso that when Y is oxygen, sulfur, sulfoxide or sufone, $R^5$ and $R^6$ are not present;

with the proviso that when Y is nitrogen, $R^6$ is not present;

with the proviso that when the broken line represents a double bond, $R^4$ and $R^6$ are not present;

with the proviso that when $R^3$ and $R^5$ are independently a substituent comprising a heteroatom when the broken line represents a double bond, the heteroatom cannot be directly bonded to positions X and Y;

with the proviso that when either the X or Y position is oxygen, sulfur, sulfoxide, sulfone or nitrogen, the other of X or Y is carbon;

with the proviso that when X or Y is defined by a heteroatom, the broken line does not represent a double bond;

with the proviso that when $R^1$, $R^2$, $R^3$, $R^4$, $R^5$, $R^6$, $R^7$, $R^8$ and $R^9$ are all defined by hydrogen or $(C_1-C_6)$ alkyl, either X or Y is oxygen, sulfur, sulfoxide, sulfone or nitrogen, or the broken line represents a double bond.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents independently selected from the group consisting of fluoro, chloro, cyano, nitro, trifluoromethyl, $(C_1-C_6)$alkoxy, $(C_6-C_{10})$aryloxy, trifluoromethoxy, difluoromethoxy and $(C_1-C_6)$alkyl.

The term "heteroaryl", as used herein, unless otherwise indicated, includes an organic radical derived from an aromatic heterocyclic compound by removal of one hydrogen, such as pyridyl, furyl, pyroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionaly substituted by 1 to 2 substituents independently selected from the group consisting of fluoro, chloro, trifluorometyl. $(C_1-C_6)$alkoxy, $(C_6-C_{10})$aryloxy, trifluoromethoxy, difluoromethoxy and $(C_1-C_6)$alkyl.

The term "acyl", as used herein, unless otherwise indicated, includes a radical of the general formula RCO wherein R is alkyl, alkoxy, aryl, arylalkyl or arylalkyloxy and the terms "alkyl" or "aryl" we as defined above.

The term "acyloxy", as used herein, includes O-acyl groups wherein "acyl" is defined above.

The positions on the ring of formula 1, as used herein, are defined as follows:

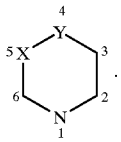

The preferred conformation of the compound of formula I includes hydroxamic acid axially disposed in the 2-position.

The compound of formula I may have chiral centers and therefore exist in different enantiomeric forms. This invention relates to all optical isomers and stereoisomers of the compounds of formula I and mixtures thereof.

Preferred compounds of formula I include those wherein Y is oxygen, nitrogen or sulfur.

Other preferred compounds of formula I include those wherein Ar is 4-methoxyphenyl or 4-phenoxyphenyl.

Other preferred compounds of formula I include those wherein $R^8$ is $(C_6-C_{10})$aryl, $(C_5-C_9)$heteroaryl, $(C_6-C_{10})$aryl$(C_1-C_6)$alkyl, $(C_5-C_9)$heteroaryl$(C_1-C_6)$alkyl, carboxylic acid carboxylic acid $(C_1-C_6)$alkyl.

Other preferred compounds of formula I include those wherein $R^2$, $R^3$, $R^6$, $R^7$ and $R^9$ are hydrogen.

More preferred compounds of formula I include those wherein Y is carbon, Ar is 4-methoxyphenyl or 4-phenoxyphenyl and $R^8$ is $(C_6-C_{10})$arylalkenyl or $(C_5-C_9)$heteroaryalkynyl.

More preferred compounds of formula I include those wherein Y is oxygen, Ar is 4-methoxyphenyl or 4-phenoxyphenyl and $R^8$ is $(C_6-C_{10})$arylalkenyl or $(C_5-C_9)$heteroarykynyl.

More preferred compounds of formula I include those wherein Y is carbon, Ar is 4-methoxyphenyl or 4-phenoxyphenyl and $R^8$ is carboxylic acid or carboxylic acid $(C_1-C_6)$alkyl.

More preferred compounds of formula I include those wherein Y is oxygen, Ar is 4-methoxyphenyl or 4-phenoxyphenyl and $R^8$ is carboxylic acid or carboxylic acid $(C_1-C_6)$alkyl.

More preferred compounds of formula I include those wherein Y is carbon, Ar is 4-methoxyphenyl or 4-phenoxyphenyl and $R^5$ is $(C_6-C_{10})$arylalkenyl or $(C_5-C_9)$heteroarylalkynyl.

More preferred compounds of formula I include those wherein Y is oxygen, Ar is 4-methoxyphenyl or 4-phenoxyphenyl and $R^5$ is $(C_6-C_{10})$arylalkenyl or $(C_5-C_9)$heteroarylalkynyl.

More preferred compounds of formula I include those wherein Y is carbon, Ar is 4-methoxyphenyl or 4-phenoxyphenyl and $R^5$ is carboxylic acid or carboxylic acid $(C_1-C_6)$alkyl.

More preferred compounds of formula I include those wherein Y is oxygen, Ar is 4-methoxyphenyl or 4-phenoxyphenyl and $R^5$ is carboxylic acid or carboxylic acid $(C_1-C_6)$alkyl.

More preferred compounds of formula I include those wherein Y is carbon, Ar is 4-methoxyphenyl or 4-phenoxyphenyl and $R^5$ is $(C_1-C_6)$alkylamino.

More preferred compounds of formula I include those wherein Y is oxygen, Ar is 4-methoxyphenyl or 4-phenoxyphenyl and $R^8$ is $(C_1-C_6)$alkylamino.

Specific preferred compounds of formula I include the following:

(2R,3S)-N-hydroxy-3ethynyl-1-(4-methoxybenzenesulfonyl)-piperidine-2-carboxamide;

(2R,3S)-N-hydroxy-1-(4-methoxybenzenesulfonyl)-3-(5-methoxythiophene-2yl-ethynyl)-piperidine-2 carboxamide;

(2R,3R)-N-hydroxy-1-(4-methoxybenzenesulfonyl)-3-(3-pyridin-3-yl-prop-2-ynyl)-piperidine2-carboxamide;

(2S,3R)-N-hydroxy-4-(4-methoxybenzonesulfonyl)-2-pyridine-3-yl-morpholine-3-carboxamide;

(2S,3R)-N-hydroxy-2-hydroxycarbamoyl-4-(4-methoxybenzenesulfonyl)-morpholine-3-carboxamide;

(2R,3R)-N-hydroxy-2-hydroxycarbamoyl-4-(4-methoxybenzenesulfonyl)-piperidine-2-carboxamide;

(2R,3S)-N-hydroxy-1-(4-methoxybenzenesulfonyl)-3-(4-phenylpyridine-2-yl)-piperidine-2-carboxamide;

(2S,3R)-N-hydroxy-1-(4-methoxybenzenesulfonyl)-2-(4-phenylpyridine-2-yl)-morpholine-2-carboxamide;

(2R,3S)-N-hydroxy-3-(2-chloro-4-fluorophenyl)-1-(4-methoxybenzenesulfonyl)-piperidine-2-carboxamide; and (2S,3R)-N-hydroxy-2-(2-chloro-4-fluorophenyl)-1-(4-methoxybenzenesulfonyl)-piperidine-3-carboxamide.

The present invention also relates to a pharmaceutical composition for (a) the treatment of a condition selected from the group consisting of arthritis, cancer, tissue ulceration, restenosis, periodontal disease, epidermolysis bullosa, scleritis and other diseases characterized by matrix metalloproteinase activity, AIDS, sepsis, septic shock and other diseases involving the production of tumor necrosis factor (TNF) or (b) the inhibition of matrix metalloproteinases or the production of tumor necrosis factor (TNF) in a mammal, including a human, comprising an amount of a compound of claim 1 or a pharmaceutically acceptable sat theeof, effective in such treatments or inhibition and a pharmaceutically acceptable carrier.

The present invention also relates to a method for the inhibition of (a) matrix metalloproteinases or (b) the production of tumor necrosis factor (TNF) in a mammal, including a human, comprising administering to said mammal an effective amount of a compound of claim 1 or a pharmaceutically acceptable salt thereof.

The present invention also relates to a method for treating a condition selected from the group consisting of arthritis, cancer, tissue ulceration, restenosis, periodontal disease, epidermolysis bullosa, scleritis and other diseases characterized by matrix metalloproteinase activity, AIDS, sepsis, septic shock and other diseases involving the production of tumor necrosis factor (TNF) in a mammal, inducing a human, comprising administering to said mammal an amount of a compound of claim 1 or a pharmaceutically acceptable sat thereof, effective in treating such a condition.

DETAILED DESCRIPTION OF THE INVENTION

The following reaction Schemes illustrate the preparation of the compounds of the present invention. Unless otherwise indicated $R^1$, $R^2$, $R^3$, $R^4$, $R^5$, $R^6$, $R^{7,}$ $R^8$, $R^9$, n and Ar in the reaction Schemes and the discussion that follow are defined as above.

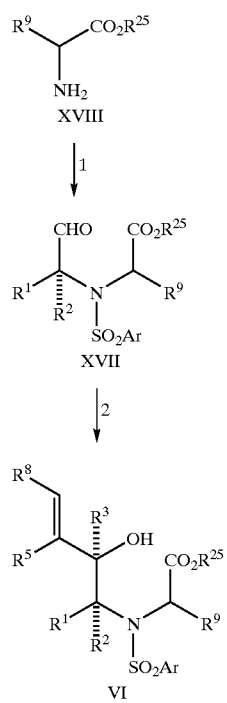

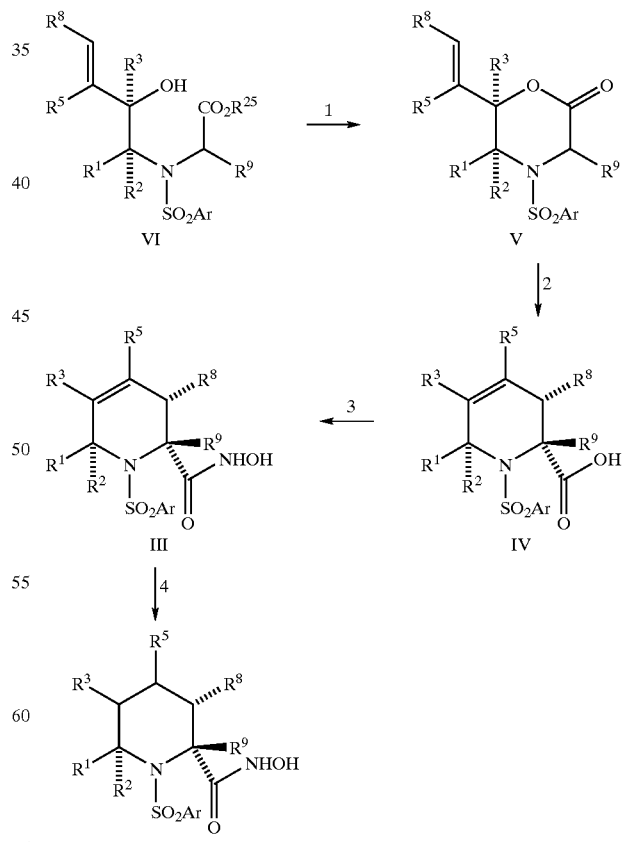

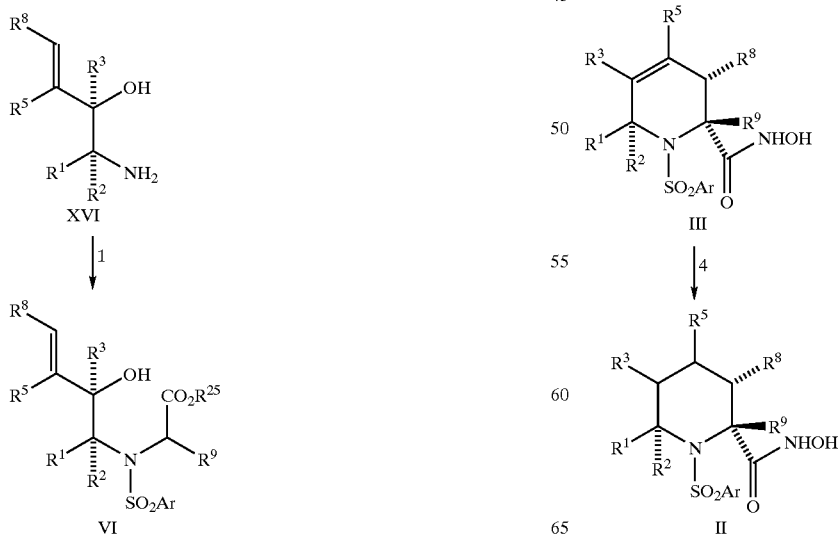

Scheme 2
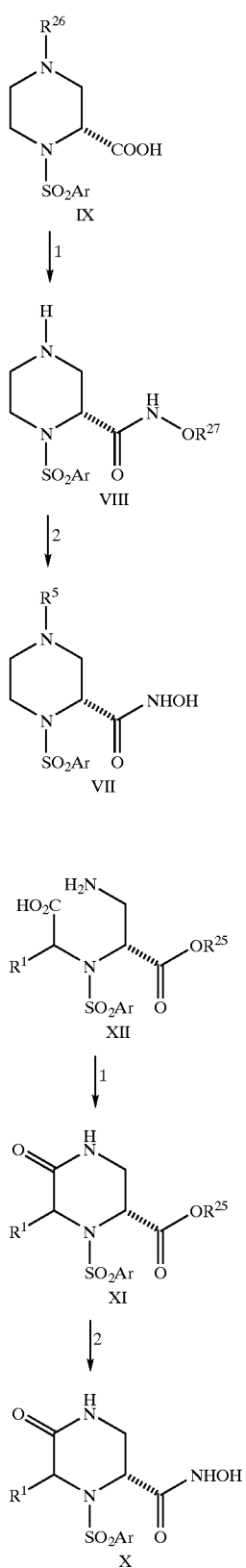
Scheme 4
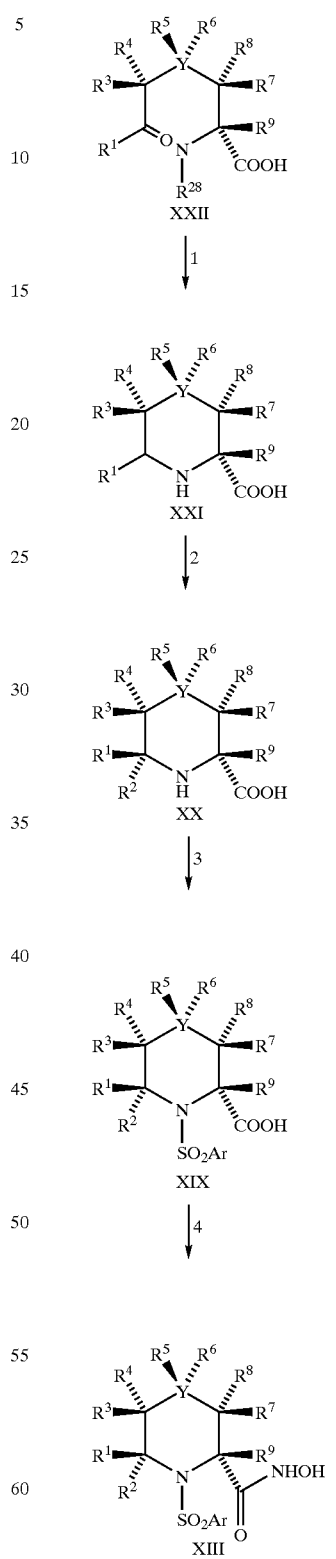

Scheme 5

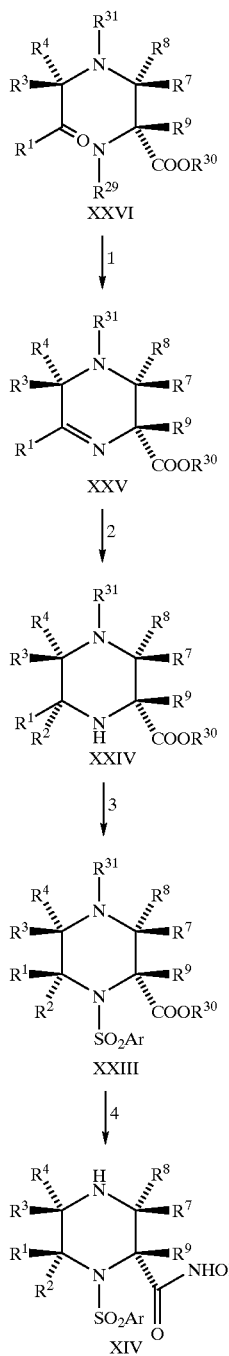

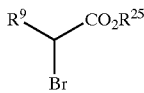

wherein $R^{25}$ is carbobenzyloxy, $(C_1-C_6)$alkyl, benzyy, allyl or tert-butyl, in the presence of sodium hexamethyidisilazane and a tetrahydrofuran-dimethylformamide solvent mixture at a temperature between about $-20°$ C. to about $20°$ C., preferably about $0°$ C., to form the hydroxy ester compound of formula VI.

In reaction 1 of Preparation 2, the amine compound of formula XVIII, wherein $R^{25}$ is as defined above, is converted to the corresponding arylsulfonyl amine compound of formula XVII by (1) reacting XVIII with an arylsulfonylhalide in the presence of triethylamine and an aprotic solvent, such as methylene chloride, tetrahydrofuran, or dioxane, at a temperature between about $20°$ C. to about $30°$ C., preferably at room temperature, (2) reacting the compound so formed with a compound of the formula

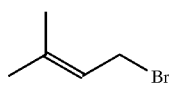

in the presence of sodium hexamethyidisilazane and a tetrahydrofuran-dimethylformamide solvent mixture at a temperature between about $-20°$ C. to about $20°$ C., preferably about $0°$ C., and (3) further reacting the compound so formed with ozone in a methylene chloride-methanol solution at a temperature between about $-90°$ C. to about $-70°$ C., preferably about $-78°$ C. The unstable ozonide compound so formed is then reacted with triphenylphosphine to form the arylsulfonyl amine compound formula XVII. In Reaction 2 of Preparation 2, the arylsulfonyl amine compound of formula XVII is converted to the corresponding hydroxy ester compound of formula VI by reacting XVII with a compound of the formula

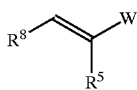

wherein W is lithium, magnesium, copper or chromium.

In reaction 1 of Scheme 1. the compound of formula VI, wherein the $R^{25}$ protecting group is carbobenzyloxy, $(C_1-C_6)$ alkyl, benzyl, allyl or tert-butyl, is converted to the corresponding morpholinone compound of formula V by lactonization and subsequent Claisen rearrangement of the compound of formula VI. The reaction is facilitated by the removal of the $R^{25}$ protecting group from the compound of formula VI is carried out under conditions appropriate for that particular $R^{25}$ protecting group in use. Such conditions include: (a) treatment with hydrogen and a hydrogenation catalyst, such as 10% palladium on carbon, where $R^{25}$ is carbobenzyloxy, (b) saponification where $R^{25}$ is lower alkyl, (c) hydrogenolysis where $R^{25}$ is benzyl, (d) treatment with a strong acid, such as trifluoroacetic acid or hydrochloric acid, where $R^{25}$ is tert-butyl, or (e) treatment with tributyitinhydride and acetic acid in the presence of catalytic bis(triphenylphosphine) palladium (II) chloride where $R^{25}$ is allyl.

In reaction 2 of Scheme 1, the morpholinone compound of formula V is converted to the carboxylic acid compound of formula IV by reacting V with lithium hexamethyidisi- In reaction 1 of Preparation 1 the compound of formula XVI is converted to the corresponding hydroxy ester compound of formula VI by first reacting XVI with an arylsulfonylhalide in the presence of trithylamine and an aprotic solvent, such as methylene chloride, tetrahydrofuran or dioxane, at a temperature between about $20°$ C. to about $30°$ C., preferably at room temperature. The compound so formed is further reacted with a compound of the formula lazane in an aprotic solvent, such as tetrahydrofuran, at a temperature between about −90° C. to about −70° C., preferably about −78° C. Trimethylsilyl chloride is then added to the reaction mixture and the solvent, tetrahydrofuran, is removed in vacuo and replaced with toluene. The resulting reaction mixture is heated to a temperature between about 100° C. to about 120° C., preferably about 110° C., and treated with hydrochloric acid to form the carboxylic acid compound of formula IV.

In reaction 3 of Scheme 1, the carboxylic acid compound of formula IV is converted to the corresponding hydroxamic acid compound of formula III by treating IV with 1-(3-dimethylaminopropyl)-3-ethylcarbodiimide and 1-hydroxybenztriazole in a polar solvent, such as dimethylformamide, followed by the addition of hydroxylamine to the reaction mixture after a time period between about 15 minutes to about 1 hour, preferably about 30 minutes. The hydroxylamine is preferably generated in situ from a salt form, such as hydroxylamine hydrochloride, in the presence of a base, such as N-methylmorpholine. Alternatively, a protected derivative of hydroxylamine or its salt form, where the hydroxyl group is protected as a tert-butyl, benzy or allyl ether, may be used in the presence of (benzotriazol-1-yloxy)tris(dimethylamino) phosphonium hexafluorphosphate and a base, such as N-methylmorpholine. Removal of the hydroxylamine protecting group is carried out by hydrogenolysis for a benzyl protecting group or treatment with a strong acid, such as trifluoroacetic acid, for a tert-butyl protecting group. The allyl protecting group may be removed by treatment with tributyttinhydride and acetic acid in the presence of catalytic bis(tiphenylphosphine) palladium (II) chloride. N,O-bis(4-methoxybenzyl)hydroxylamine may also be used as the protected hydroxylamine derivative where deprotection is achieved using a mixture of methanesulfonic acid and trifluoroacetic acid.

In reaction 4 of Scheme 1, the hydroxamic acid compound of formula III is converted, if desired, to the corresponding piperidine compound of formula II by treating III with hydrogen and a hydrogenation catayst, such a 10% palladium on carbon.

In reaction 1 of Scheme 2, the arylsulfonylpiperazine compound of formula IX, wherein $R^{26}$ is carbobenzyloxy, benzyl or carbotertbutyloxy, is converted to the compound of formula VIII by reacting IX with a protected derivative of hydroxytamine of the formula

$R^{27}ONH_2.HCl$ wherein $R^{27}$ is tert-butyl, benzyl or allyl, in the presence of dicyclohexylcarbodiimide, dimethylaminopyridine and an aprotic solvent, such as methylene chloride. The $R^{26}$ protecting group is chosen such that it may be selectively removed in the presence of an without loss of the $R^{27}$ protecting group, therefore, $R^{26}$ cannot be the same as $R^{27}$. Removal of the $R^{26}$ protecting group from the compound of formula IX is carried out under conditions appropriate for that particular $R^{26}$ protecting group in use. Such conditions include; (a) treatment with a hydrogen and a hydrogenation catalyst, such as 10% palladium on carbon, where $R^{26}$ is carbobenzyloxy, (b) hydrogenolysis where $R^{26}$ is benzyl or (c) treatment with a strong acid, such as trifluoroacefic acid or hydrochloric acid where $R^{26}$ is carbotertbutyloxy.

In reaction 2 of Scheme 2, the compound of formula VIII is converted to the corresponding hydroxamic acid compound of formula VII, wherein $R^5$ is hydrogen or $(C_1-C_6)$ alkyl, by reacting, if desired, VIII with an alkylhalide when $R^5$ is $(C_1-C_6)$alkyl. Subsequent removal of the $R^{27}$ hydroxylamine protecting group is carried out by hydrogenolysis for a benzyl protecting group or treatment with a strong acid, such as trifluoroacetic acid, for a tert-butyl protecting group. The allyl protecting group may be removed by treatment with tributyttinhydride and acetic acid in the presence of catalytic bis(triphenylphosphine) palladium (II) chloride.

In reaction 1 of Scheme 3, the aryisuffonylamine compound of formula XII, wherein $R^{25}$ is as defined above, is converted to the corresponding piperizine compound of formula XI by reacting XII with a carbodiimide and a base, such as triethylamine. The compound of formula XI is further reacted to give the hydroxamic acid compound of formula X according to the procedure described above in reaction 3 of Scheme 1.

In reaction 1 of Scheme 4, removal of the $R^{28}$ protecting group and subsequent reductive amination of the compound of formula XXII, wherein Y is oxygen, sulfur or carbon, to give the corresponding imine compound of formula XXI is carried out under conditions appropriate for that particular $R^{28}$ protecting group in use. Such conditions include those used above for removal of the $R^{26}$ protecting group in reaction 1 of Scheme 2.

In reaction 2 of Scheme 4 the imine compound of formula XXI is converted to the corresponding piperidine compound of formula XX by reacting XXI with a nucleophile of the formula $R^2M$ wherein M is lithium, magnesium halide or cerium halide. The reaction is carried out in ether solvents, such as diethyl ether or tetrahydrofuran, at a temperature between about −78° C. to about 0° C., preferably about −70° C.

In reaction 3 of Scheme 4, the sulfonation of the piperidine compound of formula XX to given the corresponding arylsullonylpiperidine compound of formula XIX is carried out by reacting XX with an arylsulfonylhalide in the presence of triethylamine and an aprotic solvent, such as metherone chloride, tetrahydrofuran or dioxane, at a temperature between about 20° C. to about 30° C., preferably at room temperature.

In reaction 4 of Scheme 4, the arylsuffonylpiperidine compound of formula XIX is converted to the hydroxamic acid compound of formula XIX according to the procedure described above in reaction 3 of Scheme 1.

In reaction 1 of Scheme 5, the compound of formula XXVI, wherein the $R^{29}$ and $R^{31}$ protecting groups are each independently selected from the group consisting of carbobenzyloxy, benzyl and carbotertbutyloxy and $R^{30}$ is carbobenzyloxy, $(C_1-C_6)$alkyl, benzyl, allyl or tert-butyl, is converted to the corresponding imine compound of formula XXV by the removal of the $R^{29}$ protecting group and subsequent reductive amination of the compound of formula XXVI. The $R^{29}$ protecting group is chosen such that it may be selectively removed in the presence of and without loss of the $R^{31}$ protecting group. Removal of the $R^{29}$ protecting group from the compound of formula XXVI is carried out under conditions appropriate for that particular $R^{29}$ protecting group in use which will not affect the $R^{31}$ protecting group. Such conditions include; (a) treatment with hydrogen and a hydrogenation catalyst, such as 10% palladium on carbon, where $R^{29}$ is carbobenzyloxy and $R^{31}$ is tert-butyl, (b) saponification where $R^{29}$ is $(C_1-C_6)$alkyl and $R^{31}$ is tert-butyl, (c) hydrogenolysis where $R^{29}$ is benzyl and $R^{31}$ is $(C_1-C_6)$ alkyl or tert-butyl, (d) treatment with a strong acid such as trifluoroacetie acid or hydrochloric acid where $R^{29}$ is tert-butyl and $R^{31}$ is $(C_1-C_6)$alkyl, benzyl or allyl, or (e) treatment with tributyttinhydride and acetic acid in the presence of catalytic bis(triphenylphosphine) palladium (II) chloride where $R^{29}$ is allyl and $R^{31}$ is $(C_1-C_6)$alkyl, benzyl or tert-butyl. The $R^{30}$ protective group may be selected such that it is removed in the same reaction step as the $R^{29}$ protecting group.

In reaction 2 of Scheme 5, the imine compound of formula XXV is converted to the corresponding compound of formula XXIV by reacting XXV with a nucleophile of the formula $R^2M$ wherein M is lithium, magnesium halide or calcium halide. The reaction is carried out in ether solvents, such as diethyl ether or tetrahydrofuran, at a temperature between about −78° C. to about 0° C., preferably about −70° C.

In reaction 3 of Scheme 5, the sulfonation of the piperidine compound of formula XXIV to give the corresponding arylsulfonylpiperidine compound of formula III is carried out according to the procedure described above in reaction 3 of Scheme 4.

In reaction 4 of Scheme 5, the arylsulfonylpiperidine compound of formula XXIII is converted to the hydroxamic acid compound of formula XIV by (1) removing the $R^{30}$, if needed, and $R^{31}$ protecting groups from XXIII followed by (2) reacting XXIII according to the procedure described above in reaction 3 of Scheme 1. Removal of the $R^{30}$ and $R^{31}$ protecting groups from the compound of formula XXIII is carried out under conditions appropriate for that particular $R^{30}$ and $R^{31}$ protecting group in use. Such conditions include those used above for removal of the $R^{25}$ protecting group in reaction 1 of Scheme 1.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium slats, such as ammonium, trimethylammonium, diethylammonium, and tris-(hydroxymethyl)methylammonium slats.

Similarly acid addition sats, such as of mineral acids, organic carboxylic and organic sulfonic acids e.g. hydrochloric acid, methanesuifonic acid, maleic acid, are also possible provided a basic group, such as pyridyl, constitutes part of the structure.

The ability of the compounds of formula I or their pharmaceutically acceptable salts (hereinafter also referred to as the compounds of the present invention) to inhibit matrix metalloproteinases or the production of tumor necrosis factor (TNF) and, consequently, demonstrate their effectiveness for treating diseases characterized by matrix metalloproteinase or the production of tumor necrosis factor is shown by the following in vitro assay tests.

Biological Assay

Inhibition of Human Collagenase (MMP-1)

Human recombinant collagenase is activated with trypsin using the following ratio: 10 μg trypsin per 100 μg of collagenase. The trypsin and collagenase are incubated at room temperature for 10 minutes then a five fold excess (50 μg/10 μg trypsin) of soybean trypsin inhibitor is added.

10 mM stock solutions of inhibitors are made up in dimethyl sulfoxide and then diluted using the following Scheme:

10 mM→120 μM→12 μM→1.2 μM→0.12 μM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D1–D6 and blanks (no enzyme, no inhibitors) are set in wells D7–D12.

Collenase is diluted to 400 ng/ml and 25 μl is then added to appropriate wells of the microfluor plate. Final concentration of collagenase in the assay is 100 ng/ml.

Substrate (DNP-Pro-Cha-Gly-Cys(Me)-His-Ala-Lys(NMA)-$NH_2$) is made as a 5 mM stock in dimethyl sulfoxide and then diluted to 20 μM in assay buffer. The assay is initiated by the addition of 50 μl substrate per well of the microfluor plate to give a final concentration of 10 μM.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine $IC_{50}$ values. The zero time is used as a blank for each compound at each concentration and these values are subtracted from the 120 minute data. Data Is plotted as inhibitor concentration vs % control (inhibitor fluorescence divided by fluorescence of collagenase alone×100). $IC_{50}$'s are determined from the concentration of inhibitor that gives a signal that is 50% of the control.

If $IC_{50}$'s are reported to be <0.03 μM then the inhibitors are assayed at concentrations of 0.3 μM, 0.03 μM, 0.03 μM and 0.003 μM.

Inhibition of Gelatinase (MMP-2)

Inhibition of gelatinase activity is assayed using the Dnp-Pro-Cha-Gly-Cys(Me)-His-Ala-Lys(NMA)-$NH_2$ substrate (10 μM) under the same conditions as inhibition of human collagenase (MMP-1).

72 kD gelatinase is activated with 1 mM APMA (p-aminophenyl mercuric acetate) for 15 hours at 4° C. and is diluted to give a final concentration in the assay of 100 mg/ml. Inhibitors are diluted as for inhibition of human collagenase (MMP-1) to give final concentrations in the assay of 30 μM, 3 μM, 0.3 μM and 0.03 μM. Each concentration is done in triplicate.

Fluorescence readings (360 nm exciation, 460 emission) are taken at time zero and then at 20 minutes intervals for 4 hours.

$IC_{50}$'s are determined as per inhibition of human collagenase (MMP-1). If $IC_{50}$'s are reported to be less than 0.03 μM, then the inhibitors we assayed at final concentrations of 0.3 μM, 0.03 μM, 0.003 μM and 0.003 μM.

Inhibition of Stromelysin Activity (MMP-3)

Inhibition of stromelysin acti is based on a modified spectrophotometric assay described by Weingarten and Feder (Weingarten, H. and Feder, J., Spectrophotometric Assay for Vertebrate Collagenase, Anal. Biochem. 147, 437–440 (1985)). Hydrolysis of the thio peptolide substrate [Ac-Pro-Leu-Gly-SCH[$CH_2CH(CH_3)_2$]CO-Leu-Gly-$OC_2H_5$] yields a mercaptan fragment that can be monitored in the presence of Eliman's reagent.

Human recombinant prostromelysin is activated with trypsin using a ratio of 1 μl of a 10 mg/ml bypsin stock per 26 μg of stromelysin. The trypsin and stromelysin are incubated at 37° C. for 15 minutes followed by 10 μl of 10 mg/ml soybean trypsin inhibitor for 10 minutes at 37° C. for 10 minutes at 37° C. to quench trypsin activity.

Assays are conducted in a totW volume of 250 μl of assay buffer (200 mM sodium chloride, 50 mM MES, and 10 mM calcium chloride, pH 6.0) in 96-well microliter plates. Activated stromelysin is diluted in assay buffer to 25 µg/ml. Ellman's reagent (3-Carboxy-4-nitrophenyl disulide) is made as a 1M stock in dimethyl formamide and diluted to 5 mM in assay buffer with 50 µl per well yielding at 1 mM final concentration.

10 mM stock solutions of inhibitors are made in dimethyl sulfoxide and diluted serially in assay buffer such that addition of 50 µL to the appropriate wells yields final concentrations of 3 µM, 0.3 µM, 0.003 µM, and 0.0003 µM. All conditions are completed in triplicate.

A 300 mM dimethyl sulfoxide stock solution of the peptide substrate is diluted to 15 mM in assay buffer and the assay is irntiated by addition of 50 µl to each well to give a final concentration of 3 mM substrate. Blanks consist of the peptide substrate and Ellman's reagent without the enzyme. Product formation was monitored at 405 nm with a Molecular Devices UVmax plate reader.

$IC_{50}$ values were determined in the same manner as for collagenase.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 µM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for Inhibition of human collagenase (MMP-1): Twenty-five microliters of each concentration is added in triplicate to the microfluor plate. The final concentrations in the assay are 30 µM, 3 µM, 0.3 µM, and 0.03 µM.

Substrate (Dnp-Pro-Cha-Gly-Cys(Me)-His-Ala-Lys (NMA)-NH$_2$) is prepared as for inhibition of human collagenase (MMP-1) and 50 µl is added to each well to give a final assay concentration of 10 µM. Fluorescence readings (360 nM excitation; 450 emission) are taken at time 0 and every 5 minutes for 1 hour.

Positive controls consist of enzyme and substrate with no inhibitor and blanks consist of substrate only.

$IC_{50}$'s are determined as per inhibition of human coliagenase (MMP-1). If $IC_{50}$'s are reported to be less than 0.03 µM, inhibitors are then assayed at final concentrations of 0.3 µM, 0.03 µM, 0.003 µM and 0.0003 µM.

Inhibition of TNF Production

The ability of the compounds or the pharmacoutcally acceptable salts thereof to inhibit the production of TNF and, consequently, demonstrate their effectiveness for treating diseases involving the production of TNF is shown by the following in vitro assay:

Human mononuclear cells were isolated from anti-coagulated human blood using a one-step Ficoll-hypaque separation technique. (2) The mononuclear cells were washed three times in Hanks balanced salt solution (HBSS) with divalent cations and resuspended to a density of $2\times10^6$/ml in HBSS containing 1% BSA. Differential counts determined using the Abbott Cell Dyn 3500 analyzer indicated that monocytes ranged from 17 to 24% of the total cells in these preparations.

180µ of the cell suspension was aliquoted into flate bottom 96 well plates (Costar). Additions of compounds and LPS (100 ng/ml final concentration) gave a final volume of 200 µl. All conditions were performed in triplicate. After a four hour incubation at 37° C. in an humidified $CO_2$ incubator, plates were removed and centrifuged (10 minutes at approximately 250×g) and the supernatants removed and assayed for TNFα using the R&D ELISA let.

For administration to humans for the inhibition of matrix metalioproteinases or the production of tumor necrosis factor (TNF), a variety of conventional routes may be used including orally, parenterally and topically. In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with varous disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is possible to administer the compounds of the present invention topically, e.g., when treating inflammatory conditions of the skin and this may be done by way of creams, jellies, gels, pastes, and ointments, in accordance with standard pharmaceutical practice.

The present invention is illustrated by the following examples, but it is not limited to the details thereof.

EXAMPLE 1

(±)-(2R*,3R*)-(N-hydroxy)-1-(4-methoxy-benzenesulfonyl)-3-methyl-1,2,3,6-tetrahydropyridine-2-carboxamide (a) To a solution of (E)-1-amino-3-pentent-2-ol (2.0 grams, 10.0 mmol) in methylene chloride (50 ml) is added triethylamine (160 μL, 11.0 mmol) followed by 4-methoxybenzenesulfonyl chloride (2.07 grams, 10.0 mmol). The mixture is stirred at room temperature for 12 hours and diluted with ethyl acetate. The mixture is washed with water, 10% citric acid, dried (sodium sulfate), filtered and concentrated. The crude product is purified by silica gel chromatography (elution with 2:1 ethyl acetate-hexanes) to provide (N-(2-hydroxy-pent-3-enyl)-4-methoxybenzenesulfonamide.

(b) To a solution of (±)-(E)-N-(2-hydroxy-pent-3-enyl)-4-methoxybenzenesulfonamide (1.2 grams, 4.42 mmol) in tetrahydrofuran-dimethylformamide (10 mL, ca. 3:1) at 0° C. is added sodium bis(trimethylsilyl)amide (4.9 mL, 1.0 M solution in torahydrofuran). After 10 minutes, t-butylbromoacetate (786 mL, 4.83 mmol) is added. The mixture is warmed to room temperature, stirred for 1 hour and quenched with saturated ammonium chloride solution. The mixture is extracted with ethyl acetate and the combined extracts are dried (sodium sulfate), filtered and concentrated. The crude product is purified by silica gel chromatography (elution with 1:1 ethyl acetate-hexanes) to provide [(2-hydroxy-pent-3-enyl)-(4-methoxybenzenesulfonyl)-amino]-acetic acid t-butyl ester.

(c) To a solution of (±)-(E)-N-(2-hydroxy-pent-3-enyl)-4-methoxybenzenesulfonyl)-amino]-acetic acid t-butyl ester (900 mg, 2.43 mmol) in benzene (10 ml) is added trifluoroacetic acid (56 μL, 0.73 mmol). The solution is heated at 80° C. for 3 hours, cooled to room temperature and concentrated to provide (±)-(E)-4-(4-methoxybenzenesulfonyl)-6-propenylmorpholin-2-one which is used without further purification.

(d) To a solution of lithium bis(trimethylsilyl)amide (2.67 mmol, 1.0 M in tetrahydrofuran) in tethydrofuran (5.0 ml) at −78° C. is added a solution of (±)-(E)-4-(4-methoxybenzenesulfonyl)-6-propenylmorpholine-2-one crude from the previous step. After 15 minutes, trimethylsilyl chloride (1.53 ml, 12.15 mmol) is added and the mixture warmed to room temperature. The solvent is removed (in vacuo) and replaced with toluene (10 ml). The resulting mixture is heated at 110° C. for 3 hours, cooled to room temperature and treated with 1N hydrochloric acid solution. After stirring for 10 minutes, the mixture is extracted with ethyl acetate and the combined extracts are dried (sodium sulfate), filtered and concentrated. The crude product is purified by silica gel chromatography (elution with 2:1 ethyl acetate-hexanes with 1% acetic acid) to provide (±)-(2R*,3R*)-1-(4-methoxy-benzenesulfonyl)-3-methyl-1,2,3,6-tetrahydropyridine-2-carboxylic acid.

(e) To a sodium of (±)-(2R*,3R*)-1-(4-methoxy-benzensufonyl)-3-methyl-1,2,3,6-tetrahydropyridine-2-carboxylic acid (100 mg, 0.36 mmol) in dimethylformamide (5 ml.) is added hydroxybentriazole (53 mg, 0.39 mmol) and 1-(3-dimethylaminopropyl)-3-ethylcarbodiimide hydrochloride (75 mg, 0.39 mmol). After 1 hour, hydroxylamine hydrochloride (75 mg, 1.08 mmol) is added followed by triethylamine (150 μL, 1.08 mmol). After stirring overnight, the mixture is diluted with water and extracted with ethyl acetate. The combined extracts are dried, filtered and concentrated. The crude product is purified by silica gel chromatography (elution with 2:1 ethyl acetate-hexanes with 1% acetic acid) to provide (±)-(2R*,3R*)-(N-hydroxy)-1-(4methoxy-benzenesulfonyl)-3-methyl-1,2,3,6-terahydropyridine-2-carboxamrde as a white solid. Melting point 173° C. (dec.). Mass spectrum (thermospray): m/Z 326 (m-C(O)N(H)OH, 100%, (m, 7%), (m+H, 30%), (m+NH$_4$, 10%). $^1$H NMR (CDCl$_3$, 250 MHz, ppm): δ7,72 (d, J=8.9 Hz, 2H), 7.03 (d, J=8.9 Hz, 2H), 5.66 (dq, J=13.0, 2.7 Hz, 1H), 5.45 (dd, 13.0, 1.9 Hz), 4.37 (d, 7.0 Hz, 1H), 4.06–3.82 (m, 2H), 3.82 (s, 3H), 3.43–3.30 (m, 1H), 2.62–231 (m, 1H), 0.97 (d, 7.5 Hz, 3H).

EXAMPLE 2

N-hydroxy-1-(4-methoxybenzenesulfonyl)-3-phenyl-1,2,3,6-tetrahydropyridine-2-carboxamide (a) To a solution of glycine t-butyl ester (5.0 grams, 29.82 mmol) In methylene chloride (50 ml) is added triethylamine (6.65 ml, 62.63 mmol) followed by 4-methoxybenzenesulfonyl chloride (29.82 mmol, 6.2 grams). The solution is stirred for 24 hours, diluted with water and extracted with ethyl acetate. The combined extracts are dried (sodium sulfate), filtered and concentrated. The crude product is purified by silica gel chromatography (elution with 6:1 hexaneyl acetate) to provide (4-methoxybenzenesulfonylamino) acetic acid t-butyl ester.

(b) To a solution of (4-methoxybenzen sulfonylamino) acetic acid t-butyl ester (3.0 grams, 10 mmol) in tetrahydrofuran-dimethylformamide (mL, ca. 3:1) at 0° C. is added sodium bis(trimethylsilyl)amide (10.0 mL 1.0 M solution in tetrahydrofuran). After 10 minutes, 4-bromo-2-methyl-2-butene (1.27 μL, 11.0 mmol) is added. The mixture is warmed to room temperature, stirred for 1 hour and quenched with saturated ammonium chloride solution. The mixture is extracted with ethyl acetate and the combined extracts are dried (sodium sulfate), filtered and concentrated. The crude product is purified by silica gel chromatography (elution with 1:1 ethyl acetate-hexanes) to provide [(4-methoxybenzenesulfonyl)-(3-methyl-but-2-enyl)-amino]-acetic acid t-butyl ester.

(c) Ozone is passed through a solution of [(4-methoxybenzenesulfonyl)-(3-methyl-but-2-enyl)-amino]-acetic acid t-butyl ester (2.0 grams, 5.4 mmol) in methylene chloride-methanol (50 mL, ca. 1:1) at −78° C. until a blue color persisted. Triphenylphosphine (4.24 grams, 16.2 mmol) is added and the resulting solution is stirred at room temperature for 3 hours. Concentration provided the crude product which is purified by silica gel chromatography (elution with 1:1 ethyl acetate-hexanes) to provide [(4-methoxybenzenesufonyl)-(2-oxo-ethyl)amino)]-acetic acid t-butyl ester.

(d) To a slurry of chromium (II) chloride (1.3 grams, 10.49 mmol) in dimethylformamide (20 ml) is added a suspension of nickel (II) chloride (0.026 mmol, 1 mg) in dimethylformamide (1 ml) followed by a mixture of (trans)-β-iodostyrene (1.20 grams, 5.24 mmol) and [(4-methoxybenzenesulfonyl)-2-oxo-athyl)-amino]acetic acid t-butyl ester (900 mg, 2.62 mmol) in dimethylformamide (5 ml). The resulting solution is stirred for three hours, diluted with water and extracted with ethyl acetate. The combined extracts are washed with brine, dried (sodium sulfate), filtered and concentrated. The crude product is purified by silica gel chromatography (elution with 3:2 hexane-ethyl acetate) to provide (±)-(E)-[(2-hydroxy-4-phenyl-but-3-enyl)-(4-methoxybenzenesulphonyl)-amino]-acetic acid t-butyl ester.

(e) (±)-(E)-[(2-hydroxy-4-phenyl-but-3-enyl)-(4-methoxybenzenesulphonyl)-amino]-acetic acid t-butyl ester is subjected to the conditions described in Example 1c. The crude product is recrystalized from chloroform to provide (±)-(E)-4-(4-methoxybenzenesulfonyl)-6-styryl-morpholin-2-one.

(f) (±)-(E)-4-(4-methoxybenzenesulfonyl)-6-morpholin-2-one is subjected to the conditions described in Example 1d. The crude product is purified by silica gel chromatography (elution with 2:1 hexane-ethyl acetate with 1% acetic acid) to provide (±)-(2R*-3R*)-1-(4-methoxybenzenesulfonyl)-3-phenyl-1,2,3,6-tetrahydropyridine-2-carboxylic acid.

(g) (±)-(2R*-3R*)-1-(4-methoxybenzenesulfonyl)-3-phenyl-1,2,3,6-tetrahydropyridine-2-caboxylic acid is subject to the conditions described in Example 1e. The crude product is purified by silica gel chromatography (elution with 1:1 hexane-ethyl acetate with 1% acetic acid) to provide N-hydroxy-1-(4-methoxybenzenesulfonyl)-3-phenyl-1,2,3,6-tetrahydropyridine-2-carboxamide as a white solid. Melting point 151–154° C. (dec.). Mass spectrum [PBMS w/C.I. (NH$_3$)]: m/Z 388 (m+NH$_4$, 100%). $^1$H NMR (CD$_3$OD) δ7.75 (d, J=8.5 Hz, 2H), 7.38–7.12 (m, 5H), 7.04 (d, J=8.5 Hz, 2H), 5.91 (d, J=8.9 Hz, 1H), 5.28 (d, J=9.9 Hz, 1H), 4.89 (s, H$_2$O), 4.57 (d, 6.8 Hz, 1H), 4.07 (ABq, JAB=18.0 Hz, Δv AB=39.1 Hz, 2H), 3.85 (o, 3H), 3.39 (bs, CD$_3$OD).

EXAMPLE 3

(±)-(2R*-3R*)-N-hydroxy-1-(4-methoxybenzesulfonyl)-3-phenyl-piperidine-2-carboxamide (a) To a solution of (±)-(2R*-3R*)-1-(4-methoxybenzenesulfonyl)-3-phenyl-1,2,3,6-tetrahydropyridine-2-carboxylic acid (65 mg, 0.17 mmol) (from Example 20), is added benzylhydroxylamine hydrochloride (32 mg, 0.20 mmol), dicyclohexylcarbodiimide (41 mg, 0.20 mmol) and dimethylaminopyridine (27 mg, 0.22 mmol). The resulting mixture is stirred overnight, diluted with ethyl acetate and filtered through Celite™ and evaporated. The crude product is purified by chromatography elution with 1:1 hexane-ethyl acetate to provide (±)-(2R*-3R*)-N-benzyloxy-1-(4-methoxybenzenesulfonyl)-3-phenyl-1,2,3,6-tetrahydropyridine-2-carboxamide.

(b) To a solution of (±)-(2R*-3R*)-N-benzyloxy-1-(4-methoxybenzenesulfonyl)-3-phenyl-1,2,3,6-tetrahydropyridie-2-caboxamide (35 mg, 0.073 mmol) in ethanol (5 ml) is added 10% palladium on carbon (10 mg, 5 mol). The flask is evacuated and backfilled with hydrogen (repeated two times). The reaction mixture is then stirred for 1 hour at which time it is filtered through Celite™ and concentrated. The product (±)-2R*-3R*)-N-hydroxy-1-(4-methoxybenzenesufonyl)-3-phenylpiperidine-2-carboxamide was collected as a white solid. Melting point 163° C. (dec). Mass spectrum [PBMS w/C.I. (NH$_3$)]: m/Z 390 (m+H$_2$), (m+NH$_4$). $^1$H NMR (CD$_3$OD) δ7.73 (d, J=8.9 Hz, 2H), 7.31–737 (m, 5H), 7.04 (d, 8.9 Hz, 2H0, 4.89 (s, H$_2$O), 4.34 (d, J=5.4 Hz, 1H), 3.86 (s, 3H), 3.74–3.63 (m, 2H), 3.31 (bs, CD$_3$OD), 2.99–2.90 (m, 1H), 2.58–2.52 (m, 1H), 1.94–1.88 (m, 1H), 1.67–160 (m, 2H).

EXAMPLE 4

(±)-N-hydroxy-1-(4-methoxybenzenesulfonyl)-2-piperazinecarboxamide hydrochloride (a) To a solution of (±)-benzyloxycarbonyl-2-piperazinecarboxylic acid (1.90 grams, 7.2 mmol) in dioxane-water (10 ml, ca. 1:1) is added 1N sodium hydroxide solution (15 ml, 15 mmol) followed by 4-methoxybenzenesulfonyl chloride. The solution is stirred for 1 hour, acidified with 1N hydrochloric acid and extracted with ethyl acetate. The combined extracts are dried (sodium sulfate), filtered and concentrated. The crude product is purified by silica gel chromatography (eluton with 2:1 ethyl acetate-hexanes with 1% acetic acid) to provide (±)-1-(4-methoxybenzenesulfonyl)-4-benzyloxycarbonyl-2-piperazinecarboxylic acid.

(b) To a solution of (±)-1-(4-methoxybenesulfonyl)-4-benzyloxycarbonyl-2-piperazinecarboxylic acid (100 mg, 0.23 mmol) in methylene chloride (5 ml) is added O-t-butylhydroxylamine hydrochloride (35 mg, 0.28 mmol), dimethylaminopyridine (37 mg, 0.30 mmol), and dicyclohexycarbodiimide (57 mg, 0.28 mmol). After stirring overnight, the reaction is diluted with hexanes and the precipitated solid filtered off. The solution is concentrated and the crude product is purified by silica gel chromatography (elution with 2:1 ethyl acetate-hexanes with 1% acetic acid) to provide (±)-N-(t-butyloxy)-1-(4-methoxybenzenesulfonyl)-4-benzyloxycarbonyl-2-piperazinecarboxamide.

(c) To a solution of (±)-N-(t-butyloxy)-1-(4-methoxybenzenesulfonyl)-4-benzyloxycarbonyl-2-piperazinecarboxamide (68 mg, 0.134 mmol), in methanol (6 ml) is added 10% palladium on carbon (7 mg). The flask is evacuated and backfilled with hydrogen (repeated 2 times). The reaction mixture is then stirred for 1 hour at which time it is filtered through Celite™ and concentrated. The product (±)-N-(butyloxy)-1-(4-methoxybenzenesulfonyl)-2-piperazinecarboxamide is used without any further purification.

(d) To a solution of (±)-N-(t-butyloxy)-1-(4-methoxybenzenesugonyl)-2-piperazinecarboxamide (30 mg, in dichloroethane is added ethanol (1 drop). The solution is cooled to −10° C. and hydrogen chloride gase is bubbled through for 5 minutes. The reaction is then sealed and stirred for 24 hours at which time the volume is reduced to ⅓ by evaporation and the precipitated solids are filtered and dried (in vacuo) to give (±)-N-hydroxy-1-(4-methoxybenzenesulfonyl)-2-piperazinecarboxamide hydrochloride as a white solid. Meiting point 167° C. (dec.). Mass spectrum (thermospray): m/Z 343 (m+1 100%). $^1$H NMR (CD$_3$OD, 250 MHz, ppm): δ7.76 (d, J=8.9 Hz, 2H), 7.07 (d, J=8.9 Hz, 2H), 3.87 (bs, H$_2$O), 4.19 (d, J=3.3 Hz, 1H), 3.87 (s, 3H), 3.58 (bd, J=6.2 Hz, 1H), 3.42 (bd, J=6.1 Hz, 1H), 3.30 (bs, CD$_3$OD), 3.16 (d, J=13.5 Hz, 1H), 2.87 (bd, J=13.3 Hz, 1H), 2.69 (dd, J=13.3, 3.0 Hz, 1H), 2.51 (dt, J=12.5, 3.8 Hz, 1H).

EXAMPLE 5

N-hydroxy-1-(4-methoxyenzenesulfonyl)-5-oxo-piperazine-2-carboxamide (a) To a solution of (±)-benzyloxycarbonylamino-2-t-butoxycarbonyl aminopropionate (2.8 grams, 7.9 mmol) in methylene chloride (25 ml) at 0° C. is added a solution of hydrochloric acid (g) dissolved in dioxane (25 ml). The solution is stirred at 0° C. for 4 hours and then concentrated. The crude product 3-benzyloxycarbonylamino-2-amino-propionic acid methyl ester hydrochloride is used without further purification.

(b) 3-benzyloxycarbonylamino-2-amino-propionic acid methyl ester hydrochloride is subjected to the conditions described in Example 1a. The crude product is purified by silica gel chromatography (elution with 1:1 hexane-ethyl acetate) to provide (±)-3-benzyloxycarbonylamino-2-(4-methoxybenzenesulfonylamino)-propionic acid methyl eter.

(c) (±)-3-benzyloxycarbonylamino-2-(4-methoxybenzene sulfonylamino)-propionic acid methyl ester is subjected to the conditions described in Example 1. The crude product is purified by silica gel chromatography (elution with 3:2 ethyl acetate-hexane to provide (±)-3-benzyloxycarbonylamino-2-[t-butoxycarbonylmethyl-(4-methoxybenzenesulfonyl) amino]-propionic acid methyl ester.

(d) (±)-3-benzyloxycarbonylamino-2-[t-butoxycarbonylmethyl-(4-methoxybenzenesulfonyl)-amino]-propionic acid methyl ester is subjected to the conditions described in Example 4c. The product 3-amino-2-[t-butoxycarbonylmethyl-(4-methoxybenzene-sulfonyl)-amino]-propionic acid methyl ester is used without further purification.

(e) To a solution of 3-amino-2-[t-butoxycarbonylmethyl-(4-methoxybenzenesulfonyl)-amino]-propionic acid methyl ester (2.46 grams, 6.1 mmol) in methylene chloride (20 ml) at 0° C. is added trifluoroacetic acid (5 ml). The solution is stirred at 0° C. for 12 hours and then concentrated. The crude product 3-amino-2-[carboxymethyl-(4-methoxybenzenesulfonyl)-amino]-propionic acid methyl ester trifluoroacetic acid salt is used without further purification.

(f) To a solution of 3-amino-2-[carboxymethyl-(4-methoxybenzenesulfonyl)-amino]propionic acid methyl ester trifluoroaoetic acid salt (2.11 grams, 6.1 mmol) in methylene chloride (5 ml) is added 1-(3-dimethylaminopropyl)-3-ethylcarbodiimide hydrochloride (1.76 grams, 9.2 mmol) and triethyamine (3.4 ml, 24.4 mmol). The resulting mixture is stirred overnight, diluted wit ethyl acetate and washed with 1N hydrochlori acid. The organic layer is dried (sodium sulfate), filtered and concentrated. The crude product is purified by silica gel chromatography (elution with ethyl acetate) to provide 1-(4-methoxybenzenesufonyl)-5-oxo-piperazine-2-carboxylic acid methyl ester.

(g) To a solution of 1-(4-methoxybenzenesufonyl)-5-oxo-piperazine-2-carboxylic acid methyl ester. (200 mg, 0.61 mmol) in methanol-tetrahydrofuran-water (5 ml, ca. 6:2:1) at 0° C. is added lithium hydroxide (64 mg, 1.53 mmol). The resulting mixture is stirred for 30 minutes, acidified with 1N hydrochloric acid and extracted with ethyl acetate. The combined extracts are dried (sodium sulfate), filtered and concentrated. The crude product 1-(4-methoxybenzonesufonyl)-5-oxo-piperazine-2-carboxylic acid is used without further purification.

(h) To a solution of 1-(4-methoxybenzenesulfonyl)-5-oxo-piperazine-2-carboxylic acid (166 mg, 0.53 mmol) in methylene chloride (5 ml) is added 0-benzyl hydroxylamine hydrochloride (255 mg, 1.6 mmol), 1-(3-dimethylaminopropyl)-3-ethylcarbodiimide hydrochloride (153 mg, 0.8 mmol) and triethylamine (370 μL 2.65 mmol). The resulting mixture is stirred overnight, diluted with ethyl acetate and washed with 1N hydrocloric acid. The organic layer is dried (sodium sulfate), filtered and concentrated. The crude product is purified by silica gel chromatography (elution with 5% methanol in methylene chloride) to provide N-(benzyloxy)-1-(4-methoxybenzenesulfonyl)-5-oxo-piperazine-2-carboxamide.

(i) N-(benzyloxy)-1-(4-methocybenzenesulfonyl)-5-oxo-piperazine-2-carboxamide is subjected to the condtions described in Example 4c to give N-hydroxy-1-(4-methoxybenzenesulfonyl)-5-oxo-piperazine-2-carboxamide as a white solid. Mass spectrum (therrnospray): m/Z 343 (m+H, 60%), (m+NH$_4$, 17%). $^1$H NMR (CD$_3$OD), 250 MHz, ppm) δ7.79 (d, J=8.9 Hz, 2H), 4.90 (s, H$_2$O), 4.47 (dd, J=5.0, 3.2 Hz, 1H), (4.03, s, 2H), 3.88 (s, 3H), 3.47 (dd, J=13.4, 3.2 Hz, 1H), 3.35–3.30 (m, 1H), 3.30 (s, CD$_3$OD)

EXAMPLE 6

N-hydroxy-1-(4-methoxybenzenesulfonyl)-morpholin-2-carboxamide (a) morpholine-2-carboxylic acid is subjected to the conditions described in Example 4a to give 1-(4-methoxybenzenesulfonyl)-morpholin-2-caboxylic acid.

(b) 1-(4-methoxybenzenesulfonyl)-morpholin-2-caboxylic acid is subjected to the conditions described in example 5h to give N-benzyloxy-1-(4-methoxybenzenesulfonyl)-morpholin-2-carboxamide.

(c) N-benzyloxy-1-(4-methoxybenzenesulfonyl)-morpholin-2-carboxamide is subjected to the conditions described in Example 4c to give N-hydroxy-1-(4-methoxybenzenesulfonyl)-morpholin-2-carboxamide as a white foam. Mass spectrum (thermospray): m/Z 343 (m+H, 100%), [α]$_D$:+57° (c=0.60, CHCl$_3$, $^1$H NMR (CDCl$_3$), 250 MHz, ppm) δ7.78 (bd, J=8.0 Hz, 2H), 7.38 (bs, 1H), 7.01 (bd, J=8.0 Hz, 2H), (4.34 (bs, J=2H), 3.87 (s, 3H), 3.85–3.30 (m, 3H), 3.30–3.15 (m, 2H).

What is claimed is:
1. A compound of the formula

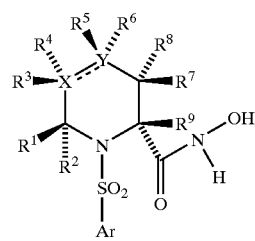

or the pharmaceutically acceptable salt thereof, wherein the broken line represents an optional double bond;

X is carbon, oxygen, sulfur, sulfoxide, sulfone or nitrogen

Y is carbon, oxygen, sulfur, sulfoxide, sulfone or nitrogen; with the proviso that if X is carbon Y is not oxygen or sulfur;

$R^1$, $R^2$ $R^3$, $R^4$ $R^5$, $R^6$, $R^7$, $R^8$ and $R^9$ are selected from the group consisting of hydrogen, (C$_1$–C$_6$)alkyl optionally substituted by (C$_1$–C$_6$)alkylamino, (C$_1$–C$_6$)alkylthio, (C$_1$–C$_6$)alkoxy, trifluoromethyl, (C$_6$–C$_{10}$)aryl, (C$_5$–C$_9$) heteroaryl, (C$_6$–C$_{10}$)arylamino, (C$_6$–C$_{10}$)arylthio, (C$_6$–C$_{10}$)aryloxy, (C$_5$–C$_9$)heteroarylamino, (C$_5$–C$_9$) heteroarylthio, (C$_5$–C$_9$)heteroaryloxy, (C$_6$–C$_{10}$)aryl (C$_6$–C$_{10}$)aryl, (C$_3$–C$_6$)cycloalkyl, hydroxy(C$_1$–C$_6$) alkyl, (C$_1$–C$_6$)alkyl(hydroxymethylene), piperazinyl, (C$_6$–C$_{10}$)aryl(C$_1$–C$_6$)alkoxy, (C$_5$–C$_9$)heteroaryl (C$_1$–C$_6$)alkoxy, (C$_1$–C$_6$)acylamino, (C$_1$–C$_6$)acylthio, (C$_1$–C$_6$)acyloxy, (C$_1$–C$_6$)alkylsulfinyl, (C$_6$–C$_{10}$) arylsulfinyl, (C$_1$–C$_6$)alkylsulfonyl, (C$_6$–C$_{10}$) arylsulfonyl, amino, (C$_1$–C$_6$)alkylamino or ((C$_1$–C$_6$) alkylamino)$_2$; (C$_2$–C$_6$)alkenyl, (C$_6$–C$_{10}$)aryl(C$_2$–C$_6$) alkenyl, (C$_5$–C$_9$)heteroaryl(C$_2$–C$_6$)alkenyl, (C$_2$–C$_6$) alkynyl, (C$_6$–C$_{10}$)aryl(C$_2$–C$_6$)alkynyl, (C$_5$–C$_9$) heteroaryl(C$_2$–C$_6$)alkynyl, (C$_1$–C$_6$)alkylamino, (C$_1$–C$_6$)alkylthio, (C$_1$–C$_6$)alkoxy, trifluoromethyl, (C$_1$–C$_6$)alkyl (difluoromethylene), (C$_1$–C$_3$)alkyl (difluoromethylene)($C_1$–$C_3$)alkyl, ($C_6$–$C_{10}$)aryl, ($C_5$–$C_9$)heteroaryl, ($C_6$–$C_{10}$)arylamino, ($C_6$–$C_{10}$)arylthio, ($C_6$–$C_{10}$)aryloxy, ($C_5$–$C_9$)heteroarylamino, ($C_5$–$C_9$)heteroarylthio, ($C_5$–$C_9$)heteroaryloxy, ($C_3$–$C_6$)cycloalkyl, ($C_1$–$C_6$)alkyl(hydroxymethylene), piperidyl, ($C_1$–$C_6$)alkylpiperidyl, ($C_1$–$C_6$)acylamino, ($C_1$–$C_6$)acylthio, ($C_1$–$C_6$)acyloxy, $R^{13}$($C_1$–$C_6$)alkyl wherein $R^{13}$ is ($C_1$–$C_6$)acylpiperazino, ($C_6$–$C_{10}$)arylpiperazino, ($C_5$–$C_9$)heteroarylpiperazino, ($C_1$–$C_6$)alkylpiperazino, ($C_6$–$C_{10}$)aryl($C_1$–$C_6$)alkylpiperazino, ($C_5$–$C_9$)heteroaryl($C_1$–$C_6$)alkylpiperazino, morpholino, thiomorpholino, piperidino, pyrrolidino, piperidyl, ($C_1$–$C_6$)alkylpiperidyl, ($C_6$–$C_{10}$)arylpiperidyl, ($C_5$–$C_9$)heteroarylpiperidyl, ($C_1$–$C_6$)alkylpiperidyl($C_1$–$C_6$)alkyl, ($C_6$–$C_{10}$)arylpiperidyl($C_1$–$C_6$)alkyl, ($C_5$–$C_9$)heteroarylpiperidyl($C_1$–$C_6$)alkyl or ($C_1$–$C_6$)acylpiperidyl;

or a group of the formula

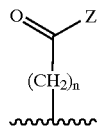

wherein n is 0 to 6;

Z is hydroxy, ($C_1$–$C_6$)alkoxy or $NR^{14}R^{15}$ wherein $R^{14}$ and $R^{15}$ are each independently selected from the group consisting of hydrogen, ($C_1$–$C_6$)alkyl optionally substituted by ($C_1$–$C_6$)alkylpiperidyl, ($C_6$–$C_{10}$)arylpiperidyl, ($C_5$–$C_9$)heteroarylpiperidyl, ($C_6$–$C_{10}$)aryl, ($C_5$–$C_9$)heteroaryl, ($C_6$–$C_{10}$)aryl($C_6$–$C_{10}$)aryl or ($C_3$–$C_6$)cycloalkyl; piperidyl, ($C_1$–$C_6$)alkylpiperidyl, ($C_6$–$C_{10}$)arylpiperidyl, ($C_5$–$C_9$)heteroarylpiperidyl, ($C_1$–$C_6$)acylpiperidyl, ($C_6$–$C_{10}$)aryl, ($C_5$–$C_9$)heteroaryl, ($C_6$–$C_{10}$)aryl($C_6$–$C_{10}$)aryl, ($C_3$–$C_6$)cycloalkyl, $R^{16}$($C_2$–$C_6$)alkyl, ($C_1$–$C_5$)alkyl($CHR^{16}$)($C_1$–$C_6$)alkyl wherein $R^{16}$ is hydroxy, ($C_1$–$C_6$)acyloxy, ($C_1$–$C_6$)alkoxy, piperazino, ($C_1$–$C_6$)acylamino, ($C_1$–$C_6$)alkylthio, ($C_6$–$C_{10}$)arylthio, ($C_1$–$C_6$)alkylsulfinyl, ($C_6$–$C_{10}$)arylsulfinyl, ($C_1$–$C_6$)alkylsulfoxyl, ($C_6$–$C_{10}$)arylsulfoxyl, amino, ($C_1$–$C_6$)alkylamino, (($C_1$–$C_6$)alkyl)$_2$amino, ($C_1$–$C_6$)acylpiperazino, ($C_1$–$C_6$)alkylpiperazino, ($C_6$–$C_{10}$)aryl($C_1$–$C_6$)alkylpiperazino, ($C_5$–$C_9$)heteroaryl($C_1$–$C_6$)alkylpiperazino, morpholino, thiomorpholino, piperidino or pyrrolidino; $R^{17}$($C_1$–$C_6$)alkyl, ($C_1$–$C_5$)alkyl($CHR^{17}$)($C_1$–$C_6$)alkyl wherein $R^{17}$ is piperidyl or ($C_1$–$C_6$)alkylpiperidyl; and $CH(R^{18})COR^{19}$ wherein $R^{18}$ is hydrogen, ($C_1$–$C_6$)alkyl, ($C_6$–$C_{10}$)aryl($C_1$–$C_6$)alkyl, ($C_5$–$C_9$)heteroaryl($C_1$–$C_6$)alkyl, ($C_1$–$C_6$)alkylthio($C_1$–$C_6$)alkyl, ($C_6$–$C_{10}$)arylthio($C_1$–$C_6$)alkyl, ($C_1$–$C_6$)alkylsulfinyl($C_1$–$C_6$)alkyl, ($C_6$–$C_{10}$)arylsulfonyl($C_1$–$C_6$)alkyl, ($C_1$–$C_6$)alkylsulfonyl($C_1$–$C_6$)alkyl, ($C_6$–$C_{10}$)arylsulfonyl($C_1$–$C_6$)alkyl, hydroxy($C_1$–$C_6$)alkyl, amino($C_1$–$C_6$)alkyl, ($C_1$–$C_6$)alkylamino($C_1$–$C_6$)alkyl, (($C_1$–$C_6$)alkylamino)$_2$($C_1$–$C_6$)alkyl, $R^{20}R^{21}NCO$($C_1$–$C_6$)alkyl or $R^{20}CO$($C_1$–$C_6$)alkyl wherein $R^{20}$ and $R^{21}$ are each independently selected from the group consisting of hydrogen, ($C_1$–$C_6$)alkyl, ($C_6$–$C_{10}$)aryl($C_1$–$C_6$)alkyl and ($C_5$–$C_9$)heteroaryl($C_1$–$C_6$)alkyl; and $R^1$ is $R^{22}O$ or $R^{22}R^{23}N$ wherein $R^{22}$ and $R^{23}$ are each independently selected from the group consisting of hydrogen, ($C_1$–$C_6$)alkyl, ($C_6C_{10}$)aryl($C_1$–$C_6$)alkyl and ($C_5$–$C_9$)heteroaryl($C_1$–$C_6$)alkyl;

or $R^{14}$ and $R^{15}$, or $R^{20}$ and $R^{21}$, or $R^{22}$ and $R^{23}$ may be taken together to form an azetidinyl, pyrrolidinyl, morpholinyl, thiomorpholinyl, indolinyl, isoindolinyl, tetrahydroquinolinyl, tetrahydroisoquinolinyl, ($C_1$–$C_6$)acylpiperazinyl, ($C_1$–$C_6$)alkylpiperazinyl, ($C_6$–$C_{10}$)arylpiperazinyl, ($C_5$–$C_9$)heteroarylpiperazinyl or a bridged diazabicycloalkyl ring selected from the group consisting of

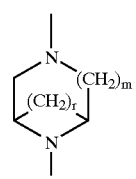

a

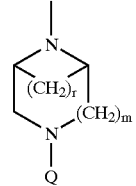

b

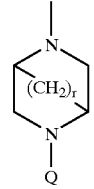

c

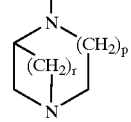

d

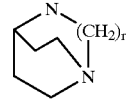

e wherein r is 1, 2 or 3;

m is 1 or 2;

p is 0 or 1; and

Q is hydrogen, ($C_1$–$C_3$)alkyl, ($C_1$–$C_6$)acyl or ($C_1$–$C_6$)alkoxy carbamoyl;

or $R^1$ and $R^2$, or $R^3$ and $R^4$, or $R^5$ and $R^6$ may be taken together to form a carbonyl;

or $R^1$ and $R^2$, or $R^3$ and $R^4$, or $R^5$ and $R^6$, or $R^7$ and $R^8$ may be taken together to form a ($C_3$–$C_6$)cycloalkyl, oxacyclohexyl, thiocyclohexyl, indanyl or tetralinyl ring or a group of the formula

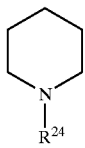

wherein

R²⁴ is hydrogen, (C₁–C₆)acyl, (C₁–C₆)alkyl, (C₆–C₁₀)aryl(C₁–C₆)alkyl, (C₅–C₉)heteroaryl(C₁–C₆)alkyl or (C₁–C₆)alkylsulfonyl; and Ar is (C₆–C₁₀)aryl or (C₅–C₉)heteroaryl, each of which may be optionally substituted by (C₁–C₆)alkyl, one or two (C₁–C₆)alkoxy, (C₆–C₁₀)aryloxy or (C₅–C₉)heteroaryloxy;

with the proviso that when R¹, R² and R⁹ are a substituent comprising a heteroatom, the heteroatom cannot be directly bonded to the 2- or 6-positions;

with the proviso that when X is oxygen or sulfur and when one or more of the group consisting of R¹, R², R⁵ and R⁶, is a substituent comprising a heteroatom, the heteroatom cannot be directly bonded to the 4- or 6-positions;

with the proviso that when Y is oxygen, sulfur, sulfoxide, sulfone or nitrogen and when one or more of the group consisting of R³, R⁴, R⁷ and R⁸, are independently a substituent comprising a heteroatom, the heteroatom cannot be directly bonded to the 3- or 5-positions;

with the proviso that when X is oxygen or sulfur, R³ and R⁴ are not present;

with the proviso that when Y is oxygen, sulfur, sulfoxide or sulfone, R⁵ and R⁶ are not present;

with the proviso that when Y is nitrogen, R⁶ is not present;

with the proviso that when the broken line represents a double bond, R⁴ and R⁶ are not present;

with the proviso that when R³ and R⁵ are independently a substituent comprising a heteroatom when the broken line represents a double bond, the heteroatom cannot be directly bonded to positions X and Y;

with the proviso that when either the X or Y position is oxygen, sulfur, sulfoxide, sulfone or nitrogen, the other of X or Y is carbon;

with the proviso that when X or Y is defined by a heteroatom, the broken line does not represent a double bond;

with the proviso that when R¹, R², R³, R⁴, R⁵, R⁶, R⁷, R⁸ and R⁹ are all defined by hydrogen or (C₁–C₆)alkyl, Ar is (C₆–C₁₀)aryl or (C₅–C₉)heteroaryl, each of which may be optionally substituted by (C₁–C₆)alkyl, one or two (C₁–C₆)alkoxy; then either X or Y is oxygen, sulfur, sulfoxide, sulfone or nitrogen, or the broken line represents a double bond.

2. A compound according to claim 1, wherein X is carbon and Y is sulfoxide, sulfone or nitrogen.

3. A compound according to claim 1, wherein at least one of said R⁷ and R⁸ is methyl.

4. A pharmaceutical composition comprising:
(a) a therapeutically effective amount of a compound as defined in claim 1 or a pharmaceutically acceptable salt thereof; and
(b) a pharmaceutically acceptable carrier, diluent, vehicle or excipient.

5. A method of treating a mammalian disease condition mediated by metalloproteinase activity which comprises administering to a mammal in need thereof a therapeutically effective amount of a compound as defined in claim 1 or a pharmaceutically acceptable salt thereof.

6. A method according to claim 5 wherein the mammalian disease condition is tumor growth, invasion or metastasis, or arthritis.

7. A method of inhibiting the activity of a metalloproteinase which comprises contacting the metalloproteinase with an effective amount of a compound as defined in claim 1 or a pharmaceutically acceptable salt thereof.

8. A method for treating cancer or AIDS in a mammal, comprising administering to said mammal an amount of a compound of the formula

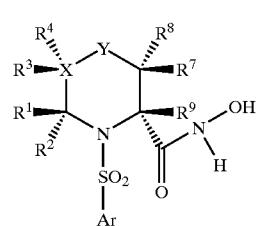

I or the pharmaceutically acceptable salt thereof, wherein

X is carbon;

Y is sulfur, or oxygen;

R¹, R² R³, R⁴, R⁷, R⁸ and R⁹ are selected from the group consisting of hydrogen, (C₁–C₆)alkyl optionally substituted by (C₁–C₆)alkylamino, (C₁–C₆)alkylthio, (C₁–C₆)alkoxy, trifluoromethyl, (C₆–C₁₀)aryl, (C₅–C₉)heteroaryl, (C₆–C₁₀)arylamino, (C₆–C₁₀)arylthio, (C₆–C₁₀)aryloxy, (C₅–C₉)heteroarylamino, (C₅–C₉)heteroarylthio, (C₅–C₉)heteroaryloxy, (C₆–C₁₀)aryl(C₆–C₁₀)aryl, (C₃–C₆)cycloalkyl, hydroxy(C₁–C₆)alkyl, (C₁–C₆)alkyl(hydroxymethylene), piperazinyl, (C₆–C₁₀)aryl(C₁–C₆)alkoxy, (C₅–C₉)heteroaryl(C₁–C₆)alkoxy, (C₁–C₆)acylamino, (C₁–C₆)acylthio, (C₁–C₆)acyloxy, (C₁–C₆)alkylsulfinyl, (C₆–C₁₀)arylsulfinyl, (C₁–C₆)alkylsulfonyl, (C₆–C₁₀)arylsulfonyl, amino, (C₁–C₆)alkylamino or ((C₁–C₆)alkyl)₂amino; (C₂–C₆)alkenyl, (C₆–C₁₀)aryl(C₂–C₆)alkenyl, (C₅–C₉)heteroraryl(C₂–C₆)alkenyl, (C₂–C₆)alkynyl, (C₆–C₁₀)aryl(C₂–C₆)alkynyl, (C₅–C₉)heteroaryl(C₂–C₆)alkynyl, (C₁–C₆)alkylamino, (C₁–C₆)alkylthio, (C₁–C₆)alkoxy, trifluoromethyl, (C₁–C₆)alkyl (difluoromethylene), (C₁–C₃)alkyl (difluoromethylene)(C₁–C₃)alkyl, (C₆–C₁₀)aryl, (C₅–C₉)heteroaryl, (C₆–C₁₀)arylamino, (C₆–C₁₀)arylthio, (C₆–C₁₀)aryloxy, (C₅–C₉)heteroarylamino (C₅–C₉)heteroarylthio, (C₅–C₉)heteroaryloxy, (C₃–C₆)cycloalkyl, (C₁–C₆)alkyl(hydroxymethylene), piperidyl, (C₁–C₆)alkylpiperidyl, (C₁–C₆)acylamino, (C₁–C₆)acylthio, (C₁–C₆)acyloxy, R¹³(C₁–C₆)alkyl wherein R¹³ is (C₁–C₆)acylpiperazino, (C₆–C₁₀)arylpiperazino, (C₅–C₉)heteroarylpiperazino, (C₁–C₆)alkylpiperazino, (C₆–C₁₀)aryl(C₁–C₆)alkylpiperazino, (C₅–C₉)heteroaryl(C₁–C₆)alkylpiperazino, morpholino, thiomorpholino, piperidino, pyrrolidino, piperidyl, (C₁–C₆)alkylpiperidyl, (C₆–C₁₀)arylpiperidyl, (C₅–C₉)heteroarylpiperidyl, (C₁–C₆)alkylpiperidyl(C₁–C₆)alkyl, (C₆–C₁₀)arylpiperidyl (C₁–C₆)alkyl, (C₅–C₉)heteroarylpiperidyl(C₁–C₆)alkyl or (C₁–C₆)acylpiperidyl;

or a group of the formula

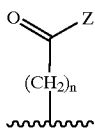

wherein n is 0 to 6;

Z is hydroxy, $(C_1-C_6)$alkoxy or $NR^{14}R^{15}$ wherein $R^{14}$ and $R^{15}$ are each independently selected from the group consisting of hydrogen, $(C_1-C_6)$alkyl optionally substituted by $(C_1-C_6)$alkylpiperidyl, $(C_6-C_{10})$arylpiperidyl, $(C_5-C_9)$heteroarylpiperidyl, $(C_6-C_{10})$aryl, $(C_5-C_9)$heteroaryl, $(C_6-C_{10})$aryl$(C_6-C_{10})$aryl or $(C_3-C_6)$cycloalkyl; piperidyl, $(C_1-C_6)$alkylpiperidyl, $(C_6-C_{10})$arylpiperidyl, $(C_5-C_9)$heteroarylpiperidyl, $(C_1-C_6)$acylpiperidyl, $(C_6-C_{10})$aryl, $(C_5-C_9)$heteroaryl, $(C_6-C_{10})$aryl$(C_6-C_{10})$aryl, $(C_3-C_6)$cycloalkyl, $R^{16}(C_2-C_6)$alkyl, $(C_1-C_5)$alkyl$(CHR^{16})(C_1-C_6)$alkyl wherein $R^{16}$ is hydroxy, $(C_1-C_6)$acyloxy, $(C_1-C_6)$alkoxy, piperazino, $(C_1-C_6)$acylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfoxyl, $(C_6-C_{10})$arylsulfoxyl, amino, $(C_1-C_6)$alkylamino, $((C_{1-C6})$alkyl$)_2$ amino, $(C_1-C_6)$acylpiperazino, $(C_1-C_6)$alkylpiperazino, $(C_6-C_{10})$aryl$(C_1-C_6)$alkylpiperazino, $(C_5-C_9)$heteroaryl$(C_1-C_6)$alkylpiperazino, morpholino, thiomorpholino, piperidino or pyrrolidino; $R^{17}(C_1-C_6)$alkyl, $(C_1-C_5)$alkyl$(CHR^{17})(C_1-C_6)$alkyl wherein $R^{17}$ is piperidyl or $(C_1-C_6)$alkylpiperidyl; and $CH(R^{18})COR^{19}$ wherein $R^{18}$ is hydrogen, $(C_1-C_6)$alkyl, $(C_6-C_{10})$aryl$(C_1-C_6)$alkyl, $(C_5-C_9)$heteroaryl$(C_1-C_6)$alkyl, $(C_1-C_6)$alkylthio$(C_1-C_6)$alkyl, $(C_6-C_{10})$arylthio$(C_1-C_6)$alkyl, $(C_1-C_6)$alkylsulfinyl$(C_1-C_6)$alkyl, $(C_6-C_{10})$arylsulfinyl$(C_1-C_6)$alkyl, $(C_1-C_6)$alkylsulfonyl$(C_1-C_6)$alkyl, $(C_6-C_{10})$arylsulfonyl$(C_1-C_6)$alkyl, hydroxy$(C_1-C_6)$alkyl, amino$(C_1-C_6)$alkyl, $(C_1-C_6)$alkylamino$(C_1-C_6)$alkyl, $((C_1-C_6)$alkyl$)_2$amino $(C_1-C_6)$alkyl, $R^{20}R^{21}NCO(C_1-C_6)$alkyl or $R^{20}OCO(C_1-C_6)$alkyl wherein $R^{20}$ and $R^{21}$ are each independently selected from the group consisting of hydrogen, $(C_1-C_6)$alkyl, $(C_6-C_{10})$aryl$(C_1-C_6)$alkyl and $(C_5-C_9)$heteroaryl$(C_1-C_6)$alkyl; and $R^{19}$ is $R^{22}O$ or $R^{22}R^{23}N$ wherein $R^{22}$ and $R^{23}$ are each independently selected from the group consisting of hydrogen, $(C_1-C_6)$alkyl, $(C_6-C_{10})$aryl$(C_1-C_6)$alkyl and $(C_5-C_9)$heteroaryl$(C_1-C_6)$alkyl;

or $R^{14}$ and $R^{15}$, or $R^{20}$ and $R^{21}$, or $R^{22}$ and $R^{23}$ may be taken together to form an azetidinyl, pyrrolidinyl, morpholinyl, thiomorpholinyl, indolinyl, isoindolinyl, tetrahydroquinolinyl, tetrahydroisoquinolinyl, $(C_1-C_6)$acylpiperazinyl, $(C_1-C_6)$alkylpiperazinyl, $(C_6-C_{10})$arylpiperazinyl, $(C_5-C_9)$heteroarylpiperazinyl or a bridged diazabicycloalkyl ring selected from the group consisting of

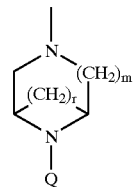
a

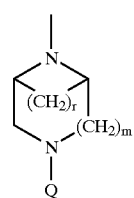
b

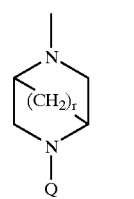
c

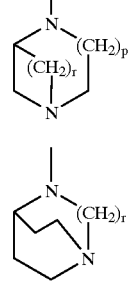
d

e wherein r is 1, 2 or 3;

m is 1 or 2;

p is 0 or 1; and

Q is hydrogen, $(C_1-C_3)$alkyl, $(C_1-C_6)$acyl or $(C_1-C_6)$alkoxy carbanoyl;

or $R^1$ and $R^2$, or $R^3$ and $R^4$, may be taken together to form a carbonyl;

or $R^1$ and $R^2$, or $R^3$ and $R^4$, or $R^7$ and $R^8$ may be taken together to form a $(C_3-C_6)$cycloalkyl, oxacyclohexyl, thiocyclohexyl, indanyl or tetralinyl ring or a group of the formula

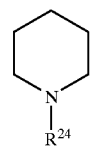

wherein $R^{24}$ is hydrogen, $(C_1-C_6)$acyl, $(C_1-C_6)$alkyl, $(C_6-C_{10})$aryl$(C_1-C_6)$alkyl, $(C_5-C_9)$heteroaryl$(C_1-C_6)$alkyl or $(C_1-C_6)$alkylsulfonyl; and Ar is $(C_6-C_{10})$aryl or $(C_5-C_9)$heteroaryl, each of which may be optionally substituted by $(C_1-C_6)$alkyl, one or two $(C_1-C_6)$alkoxy, $(C_6-C_{10})$aryloxy or $(C_5-C_9)$heteroaryloxy;

with the proviso that $R^7$ is other than hydrogen only when $R^8$ is other than hydrogen;

with the proviso that $R^3$ is other than hydrogen only when $R^4$ is other than hydrogen;

with the proviso that $R^2$ is other than hydrogen only when $R^1$ is other than hydrogen;

with the provisio that when $R^1$, $R^2$ and $R^9$ are a substituent comprising a heteroatom, the heteroatom cannot be directly bonded to the 2- or 6-positions;

with the proviso that when one or more of the group consisting of $R^3$, $R^4$, $R^7$ and $R^8$, are independently a substituent comprising a heteroatom, the heteroatom cannot be directly bonded to the 3- or 5-positions.

\* \* \* \* \*